(12) United States Patent
Takami et al.

(10) Patent No.: US 6,193,649 B1
(45) Date of Patent: Feb. 27, 2001

(54) ENDOSCOPE AIR SENDING DEVICE

(75) Inventors: Satoshi Takami, Saitama; Junji Usami; Hidehito Kurosawa, both of Tokyo, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/391,350

(22) Filed: Sep. 8, 1999

(30) Foreign Application Priority Data

Sep. 11, 1998 (JP) .................................................. 10-258477

(51) Int. Cl.⁷ .............................. A61B 1/12; A61M 31/00
(52) U.S. Cl. ............................................. 600/158; 600/560
(58) Field of Search ............................. 600/560, 156, 600/158, 159

(56) References Cited

U.S. PATENT DOCUMENTS

| | | | | |
|---|---|---|---|---|
| 3,726,272 | * | 4/1973 | Fukami et al. | 600/126 |
| 3,730,645 | * | 5/1973 | Mashakaru et al. | 417/12 |
| 4,548,197 | * | 10/1985 | Kinoshita | 600/158 |
| 4,550,716 | * | 11/1985 | Kinoshita | 600/158 |
| 4,552,130 | * | 11/1985 | Kinoshita | 600/158 |
| 4,971,034 | | 11/1990 | Doi et al. | 600/158 |
| 5,133,336 | * | 7/1992 | Savitt et al. | 600/132 |
| 5,249,579 | * | 10/1993 | Hobbs et al. | 600/458 |
| 5,377,688 | | 1/1995 | Aviv et al. | 600/560 |
| 5,515,860 | | 5/1996 | Aviv et al. | 600/560 |
| 5,676,155 | * | 10/1997 | Novak et al. | 600/560 |

FOREIGN PATENT DOCUMENTS 8-512219   12/1996   (JP) .

* cited by examiner

*Primary Examiner*—Cary O'Connor
*Assistant Examiner*—Charles Marmor, II
(74) *Attorney, Agent, or Firm*—Greenblum & Bernstein, P.L.C.

(57) ABSTRACT

Inside an endoscope air sending device (15), an air compressor (13), an air tank (34), an air filter (35), a pressure control valve (38), a pressure sensor (14), and a discharge valve (12) are provided so that those elements form a closed space therein. An air sending fan (47) is provided on the wall of a housing (10), and a circuit board (K) is provided above the air sending fan (47) and those elements forming the closed space. A discharge outlet (60) is provided on the housing (10) in such a manner that the discharge outlet (60) is located above the circuit board (K).

6 Claims, 5 Drawing Sheets

ENDOSCOPE AIR SENDING DEVICE

BACKGROUND OF THE INVENTION

This invention relates to an endoscope air sending device for sending air into a body cavity such as the stomach, and more particularly to the arrangement of components, which prevents an unwanted rise of temperature in the endoscope air sending device.

An endoscope air sending device is known in the art which is so designed that the air whose pressure is increased by an air compressor is discharged by controlling a valve, and the air thus discharged is sent into the body cavity through a tube. In the device, a pressure control valve is provided to control the pressure of the air to be discharged. The pressure control valve adjusts the sectional area of the air flowing path, to thereby control the pressure of the air.

The pressure control valve is only able to decrease the pressure of the air to be discharged. Therefore, it is necessary to provide a large compressor of high output type which can send a high pressure air. Hence, during the medical operation, the compressor operating at all times makes a noise. Furthermore, because of the structure of the pressure control valve, the endoscope air sending device cannot discharge the air with fine pressure adjustment. The endoscope air sending device cannot accurately perform the air pressure control over a wide range of from low pressure to high pressure.

SUMMARY OF THE INVENTION

Accordingly, an object of the invention is to provide an endoscope air sending device which defines a closed space for accurate pressure control to obtain various air discharge pressures, and which prevents the air in the closed space from being greatly changed in temperature to provide stable pressure control.

The foregoing object of the invention has been achieved by the provision on an endoscope air sending device which, according to the invention comprises:

a compressor which compresses air and sends the air thus compressed into a closed space;

an air tank which is a part of the closed space;

an air filter which removes dust from the closed space;

a pressure sensor which measures a pressure of the air in the closed space;

a pressure control valve which discharges the air from the closed space to adjust the pressure of the air in the closed space according to a pressure measured by the pressure sensor;

a discharge valve which discharges the air from the closed space;

an air sending fan which supplies air from outside of the endoscope air sending device to members forming the closed space;

a circuit board on which circuits for transmitting electrical signals to the compressor, the pressure sensor, the pressure control valve, and the discharge valve are provided; and a discharge outlet through which the air heated by the circuit board is discharged, and wherein the air sending fan, the compressor, the air tank, the air filter, the pressure sensor, the pressure control valve, and the discharge valve are provided below the circuit board, with the discharge outlet provided above the circuit board.

In the endoscope air sending device, it is desirable that the closed space is formed by communicating the members with one another which are the compressor, a first air tube which connects the compressor and the air tank to each other, the air tank, a second air tube which connects the air tank and the air filter to each other, the air filter, a third air tube which connects the air filter and the discharge valve to each other, a fourth air tube which connects the third air tube and the pressure control valve to each other, the pressure control valve, a fifth air tube which connect the third air tubes to the pressure sensor, the pressure sensor, and the discharge valve.

In the device, it is desirable that the third air tube is communicated through couplings with the fourth air tube and the fifth air tube.

Furthermore, it is desirable that the circuit board is supported by board supports.

Moreover, it is desirable that the discharge outlet is provided away from the air sending fan with respect to the closed space.

In addition, it is desirable that the air sending fan is provided beside the compressor.

The present disclosure relates to the subject matter contained in Japanese patent application No. Hei. 10-258477 (filed on Sep. 11, 1998), which is expressly incorporated herein by reference in its entirety.

DESCRIPTION OF THE PREFERRED EMBODIMENT

Figure 1:
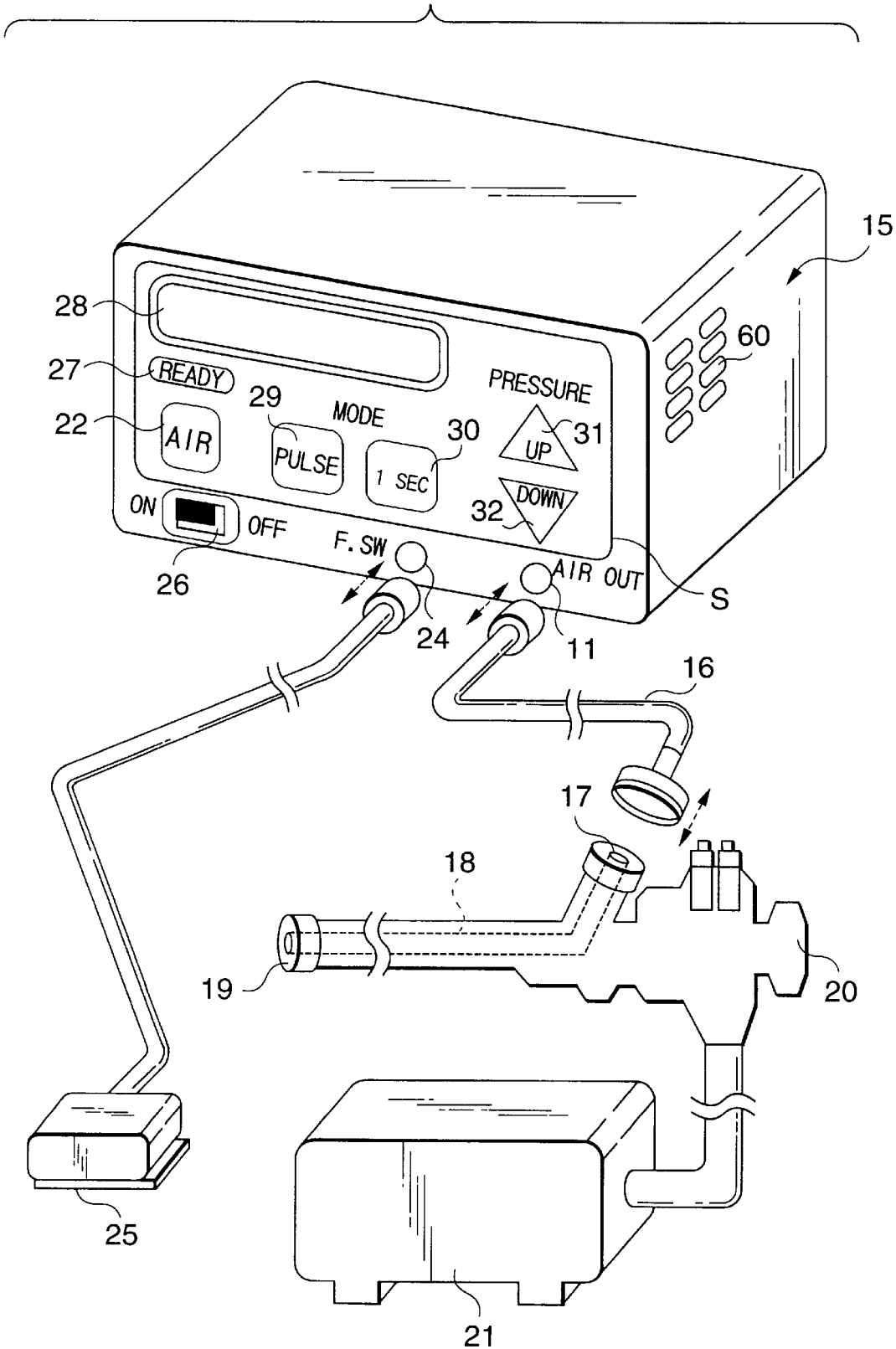
FIG. 1 is a perspective view of an endoscope air sending device, which constitutes a preferred embodiment of the invention.

An embodiment of the invention will be described with reference to the accompanying drawings. FIG. 1 is a perspective view of an endoscope air sending device, which constitutes the embodiment of the invention. The endoscope air sending device is to send air into a body cavity such as the stomach for inspection of the affected part.

The endoscope air sending device 15 is provided at its front surface with an operating panel S, a main switch 26, and connectors 11 and 24. The operating panel S has pressure setting switches and other various switches. A discharging outlet 60 for adjusting the temperature within the endoscope air sending device 15 is formed on the side wall of the device 15.

The main switch 26 is to supply current to an electrical circuit in the device 15. A discharging switch 22 is to discharge air from a closed space formed in the device 15. More specifically, when the discharging switch 22 is turned on, the air is discharged through the connector 11. A lamp 27 is to display, when the pressure of the air in the closed spaced reaches a predetermined value, the fact that the air discharging operation has become ready.

A display section 28 displays a value of an air pressure to be set.

A pulse switch 29 is to discharge the air in a pulse mode. A one-second switch 30 is to discharge the air for one second. An up switch 31 and a down switch 32 are to set the pressure of the closed spaced.

The connector 11 is connected to a connecting tube 16, so that, as the air is discharged, the air is sent into the body cavity through the connecting tube 16. The connector 24 is connected to the power supply cord of a foot switch 25 so that the remote control of the air discharging operation is enabled.

The other end of the connecting tube 16 (which is not connected to the connector 11) is connected to a forceps inlet 17 of an endoscope 20. The forceps inlet 17 is communicated through a forceps channel 18 to a forceps outlet 19. A path for allowing the air to flow is defined between the connector 11 and the forceps outlet 19, so that the air discharged from the connector 11 is sent through the forceps outlet 19 into the body cavity. The image of the body cavity is formed on an image pickup element (not shown) provided within an endoscope 20, and displayed on a monitor (not shown) in an animation mode with the aid of a processor 21.

Figure 2:
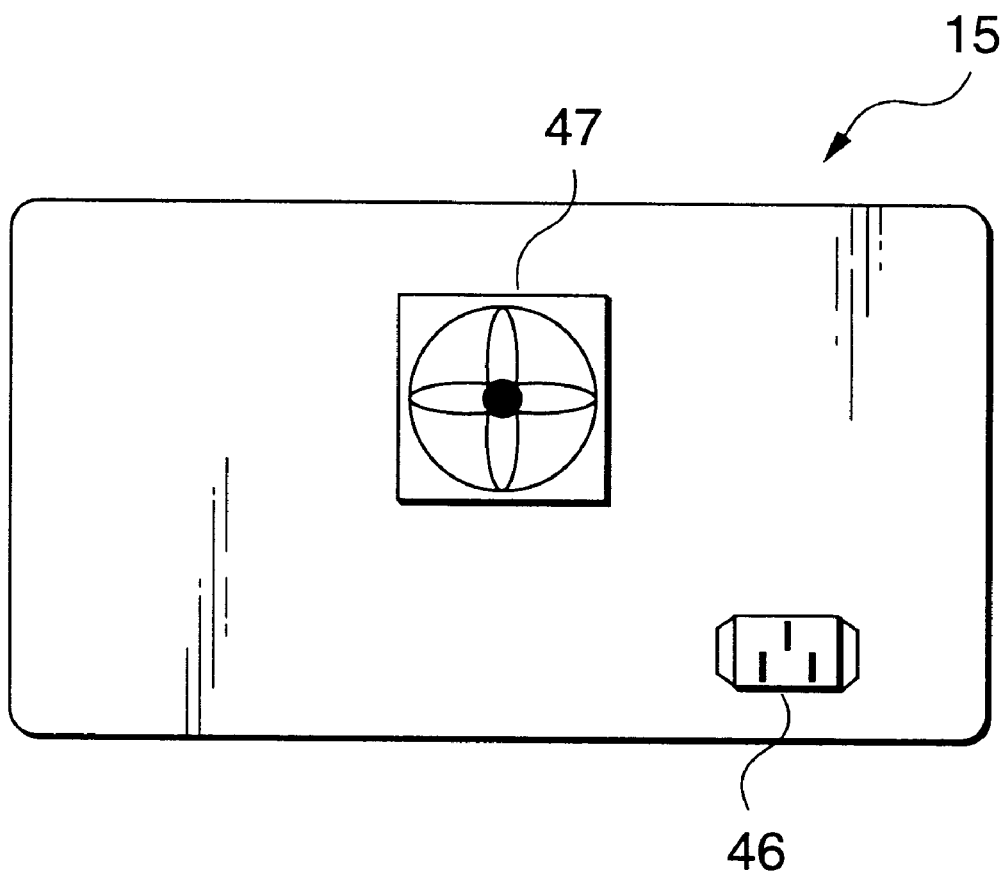
FIG. 2 is a rear view of the endoscope air sending device.

FIG. 2 is a rear view of the endoscope air sending device 15.

A DC fan (an air sending fan) 47 for supplying air to the inside of the endoscope air sending device 15 is provided in the rear of the endoscope air sending device 15. The DC fan is kept operated when the power switch is ON. An AC inlet 46 through which current is received from the commercial power source is provided as shown in FIG. 2.

Figure 3:
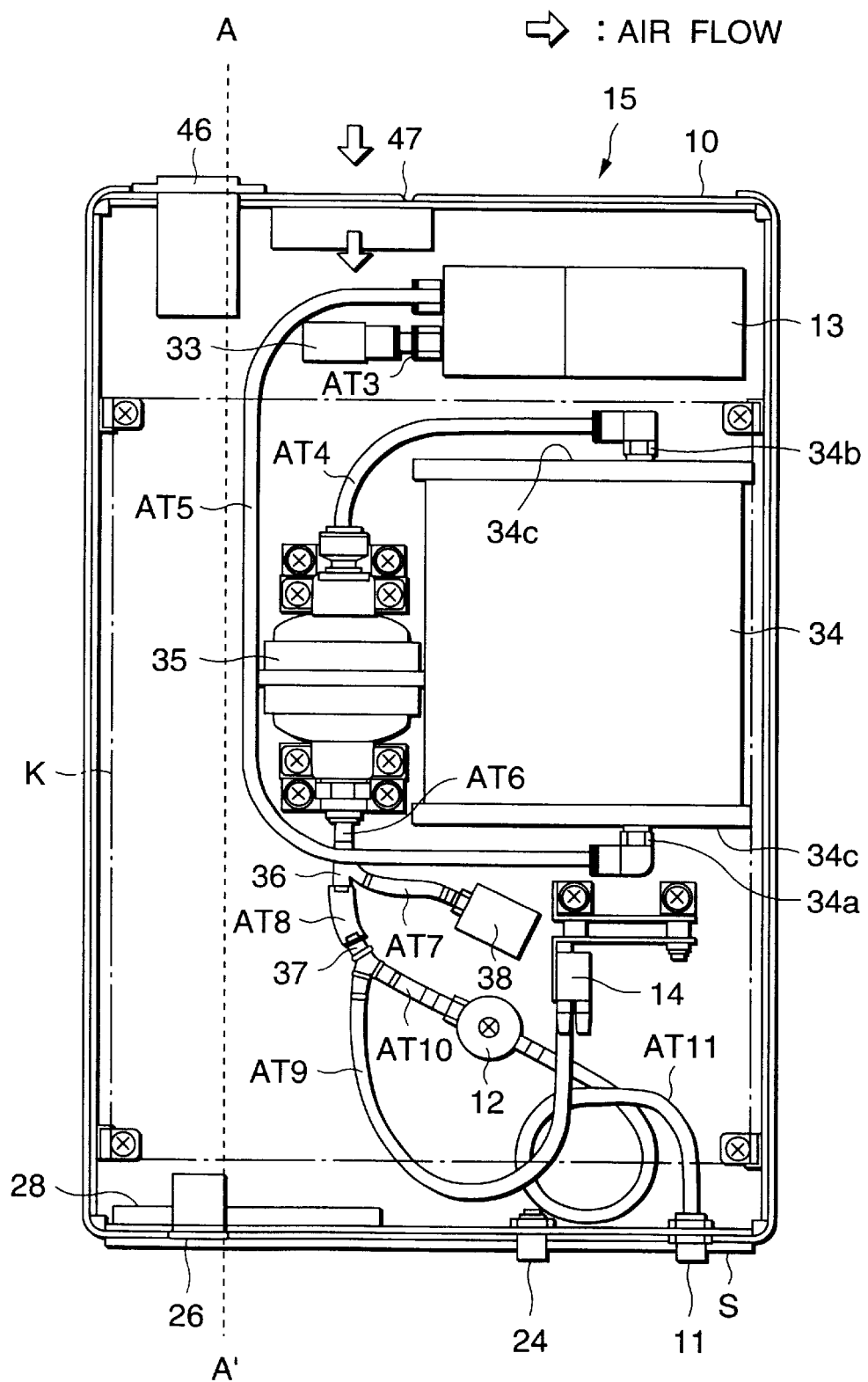
FIG. 3 is a plan view of the inside of the endoscope air sending device.

FIG. 3 is a top view showing the arrangement of essential components (except the electrical circuit and the wiring) inside the endoscope air sending device 15.

The AC inlet 46, the DC fan 47, the main switch 26, the operating panel S including the display section 28, and the connectors 11 and 24 are arranged on the walls of the housing 10.

Various members for discharging the air are provided on the bottom of the housing 10, while a circuit board K is set over those members. In the embodiment, the circuit board K substantially covers almost all the members in the housing 10; however, the circuit board K may be smaller in area than shown. A circuit for transmitting electrical signals to the members is provided on the circuit board K.

The closed space for discharging air is formed inside the housing 10. This closed space is formed by the compressor 13, an air tube AT5 (a first air tube), an air tank 34, an air tube AT4 (a second air tube), an air filter 35, an air tube AT6 (a third air tube), a coupling 36, an air tube AT7 (a fourth air tube), a pressure control valve 38, an air tube AT8 (the third air tube), a coupling 37, an air tube AT9 (a fifth air tube), a pressure sensor 14, an air tube AT10 (the third air tube) and a discharge valve 12 which are communicated with one another. The air in the closed space is discharged through an air tube AT11 from the connector 11.

The closed space is branched towards the pressure control valve 38 by the coupling 36 and the air tube AT7, and towards the pressure sensor 14 by the coupling 37 and the air tube AT9. The coupling 36 is to communicate the air tube AT6, the air tube AT7, and the air tube AT8 with one another, and the coupling 37 is to communicate the air tube AT8, the air tube AT10, and the air tube AT9 with one another. The air tubes are pipes through which air flows.

In the case where the pressure of the closed space is adjusted or the air in the closed space is discharged, the air in the closed space is sent outside thereof. The pressure control valve 38 is normally closed, but opened when the pressure of the air in the closed space is decreased. The discharge valve 12 is normally closed, but opened when the discharging switch 22 or the foot switch 25 is operated.

A silencer 33 for decreasing the volume of noise made when the compressor is in operation, is connected through the air tube AT3 to the air suction inlet (not shown) of the compressor 13. When the compressor 13 is operated, the air flowing in through the silencer 33 and the air tube AT3 is compressed, and sent into the closed space, whereby the pressure of the air in the closed space is increased. The silencer 33 also has a filter function to remove dust mixed in the air to be supplied to the compressor 13.

The air tank 34 is provided for the purpose of increasing the volume of the closed space. The volume of the air tank 34 is much larger than the total volume of the air tubes AT4 through AT10. On the end surfaces 34*c* of the air tank 34, connectors 34*a* and 34*b* are provided to which the air tubes AT5 and AT4 are connected, respectively. The air tube AT5 is connected to the connector 34*a* which is located farther from the air compressor 13 than the connector 34*b*.

The air filter 35 is provided to remove dust from the air in the closed space. The pressure of the air in the closed space is measured with the pressure sensor 14.

The pressure control valve 38 discharges the air to set the pressure of the closed space as required, thereby adjusting the pressure of the closed space. When it is determined that the pressure of the closed space measured by the pressure sensor 14 is lower than the set value (pressure), the compressor 13 operates, and the pressure control valve 38 is closed. In this case, the pressure control valve 38 and the discharge valve 12, both being closed, secure the sealed closed space, and thus no air leakage from the closed space occurs. Hence, the pressure within the closed space can quickly reach the set value for the air pressure. When it is determined that the pressure of the closed space is higher than the set value, the compressor 13 is stopped, and the pressure control valve 38 is opened. In the case where the pressure of the closed space is equal to the set value, the compressor 13 is not operated (stopped), and the pressure control valve 38 is closed. In this case, the pressure control valve 38 and the discharge valves 12 are both closed to secure the sealed closed space, to thereby maintain the air pressure within the closed space at the set value until the discharge valve 12 is opened.

When the discharging switch 22 or the foot switch 25 is operated, the discharge valve 12 is operated. When the discharge valve 12 is opened, the air is discharged through the air tube AT11 from the connector 11.

Figure 4:
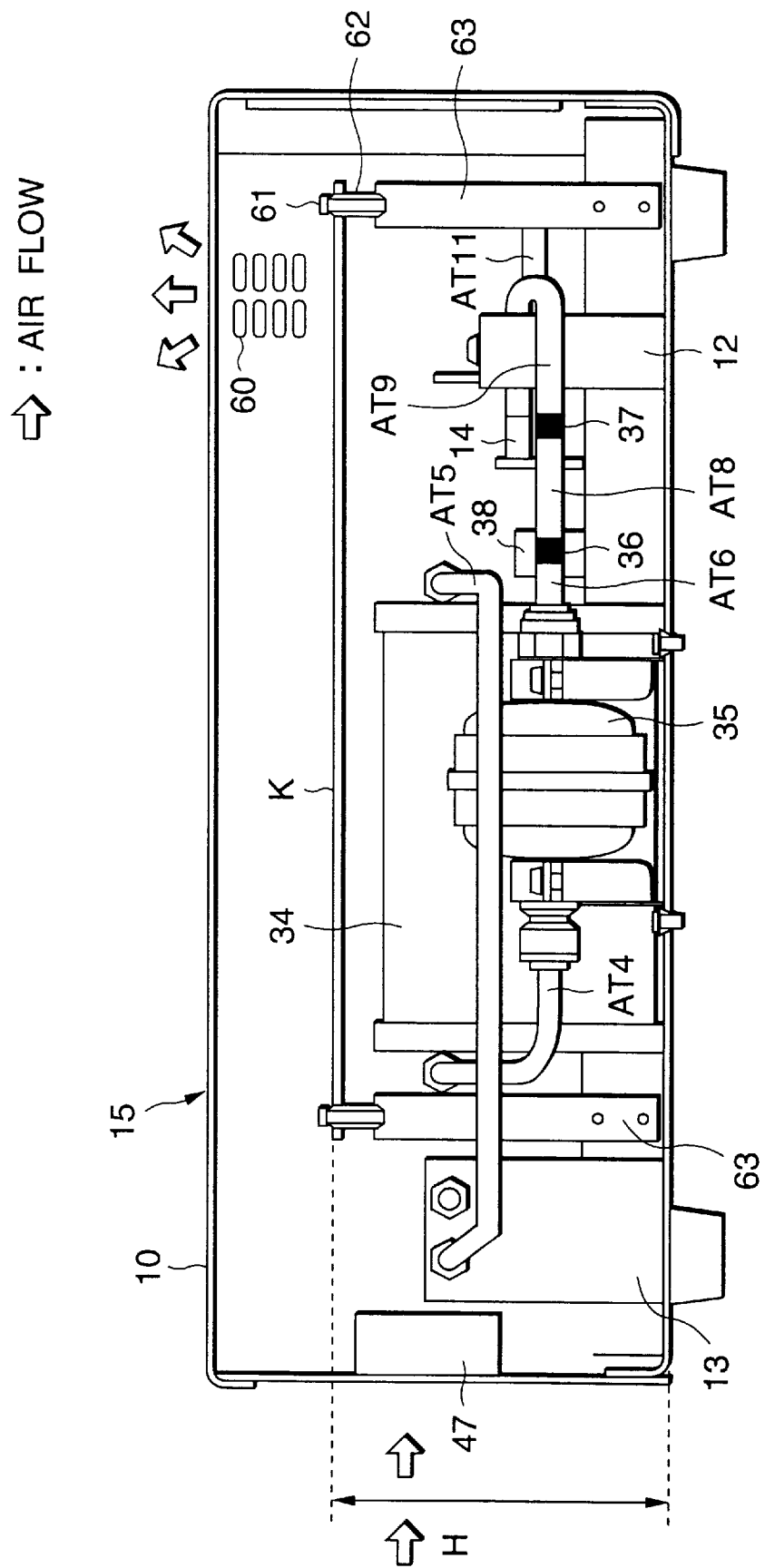
FIG. 4 is a sectional view of the endoscope air sending device.

FIG. 4 is a sectional view of the endoscope air sending device 15 taken along line A–A' of FIG. 3.

The DC fan 47 is provided below the circuit board K; that is, the position of the DC fan 47 is lower than the height H of the circuit board K. Therefore, to the members forming the closed space, the air sucked by the DC fan 47 from outside is supplied.

The circuit board K is supported by board supports 63; that is, four board supports 63 are arranged at four corners of the circuit board K. However, it should be noted that the number of board supports 63 depends on the size and configuration of the circuit board K, and may be changed. Each of the board supports 63 has a threaded hole (not shown), with which a screw 61 is engaged through a spacer 62, whereby the circuit board K is secured.

The discharge outlet 60 is formed in the side wall of the housing 10 so as to avoid the interference with the operations of the switches on the front surface. The position of the discharge outlet 60 is far from the DC fan 47 and is higher than the height H of the circuit board K. The discharge outlet 60 is made up of horizontal slits arranged in two columns.

Figure 5:
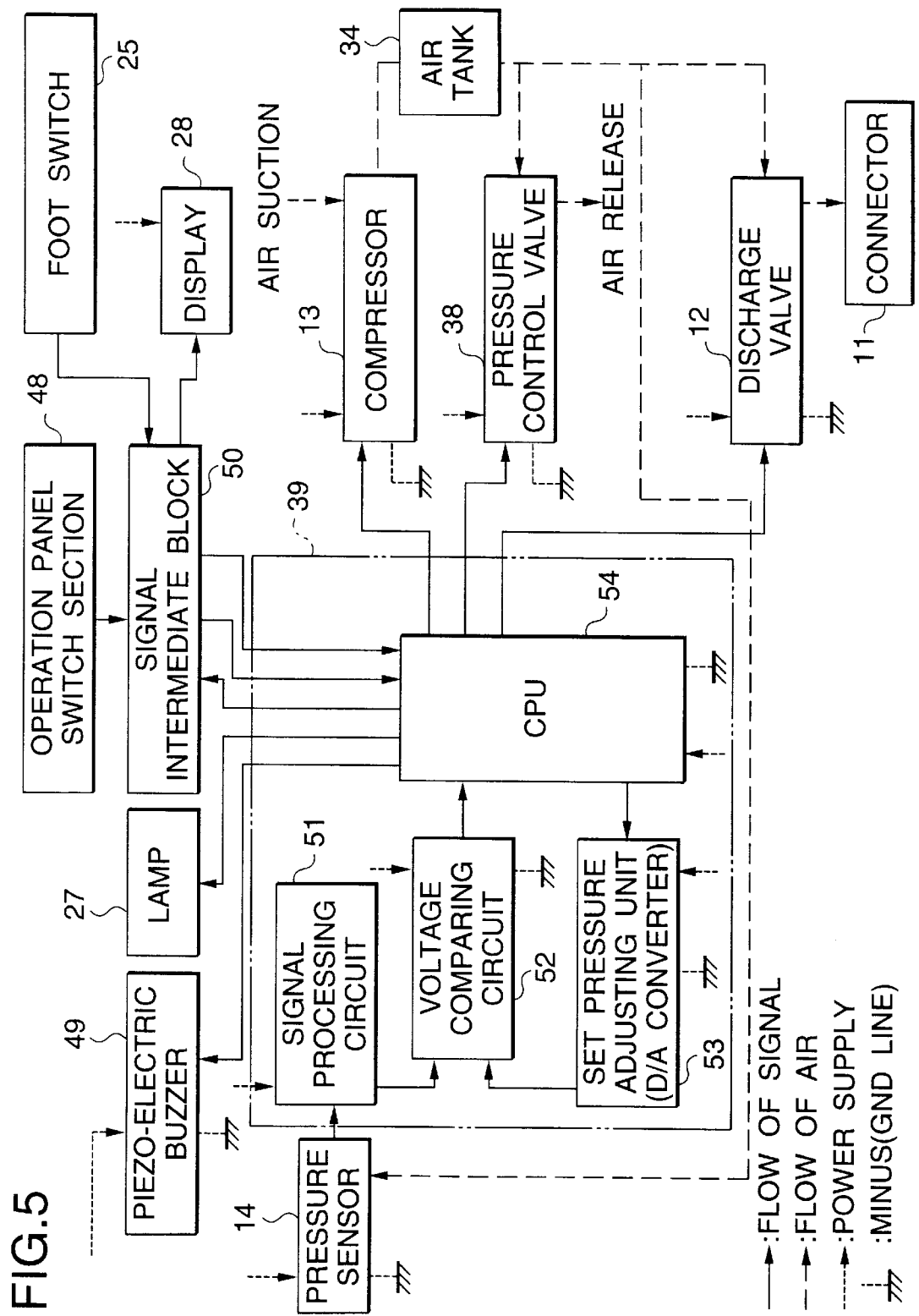
FIG. 5 is a block diagram showing an electrical circuit in the endoscope air sending device.

FIG. 5 is a block diagram showing the electrical circuit of the embodiment.

A control circuit 39 comprises a signal processing circuit 51, a voltage comparison circuit 52, a set pressure adjusting unit 53, and a CPU 54, and controls the whole operation of the endoscope air sending device 15. The CPU 54 outputs drive signals to apiezo-electric buzzer 49, the lamp 27, the compressor 13, the pressure control valve 38, and the discharge valve 12.

The operating panel switch section 48 generates signals upon the operation of the discharge switch 22, the pulse switch 29, the one-second switch 30, the up switch 31 and the down switch 32. The signals outputted by the operating panel switch section 48 and the foot switch 25 are transmitted through a signal intermediate block 50 to the CPU 54. In the signal intermediate block 50, the signals transmitted from the operating panel switch 48 are subjected to predetermined processes, or converted into signals which can be handled by the CPU 54. The signal concerning the pressure which has been set by the operations of the up switch 31 and the down switch 32 is applied through the signal intermediate block 50 to the display section 28.

The output signal of the pressure sensor 14 is inputted to the signal processing circuit 51, where it is processed for instance to remove noise therefrom. The signal thus processed is applied to the voltage comparison circuit 52. On the other hand, according to the signal concerning the set pressure which is inputted to the CPU by the operations of the up switch 31 and the down switch 32, a digital signal is applied to the set pressure adjusting unit 53 (a D/A converter). The digital signal is converted into an analog signal by the set pressure adjusting unit 53, which is then transmitted to the voltage comparison circuit 52.

The voltage comparison circuit 52 compares the signal from the signal processing circuit 51 with the signal (voltage signal) from the set pressure adjusting unit 53. A signal generated as a result of the comparison is converted into a signal of a certain voltage level, which can be handled by the CPU 54, and then transmitted to the CPU 54. The CPU 54 judges whether or not the pressure of the air in the closed space is equal to the set pressure based on the signal transmitted from the voltage comparison circuit 52.

In the case where the voltages compared with each other by the voltage comparison circuit 52 are substantially equal to each other, such a hunting operation may occur that the start and stop of the compressor 13 and the opening and closing of the pressure control valve 38 are repeated. In order to eliminate such hunting operation, a dead voltage zone or non-sensible voltage zone is preliminarily set for the comparison voltage range.

The piezo-electric buzzer 49 generates a buzzer sound in response to each switch operation. When the air discharging operation is ready, the lamp 27 is turned on.

Electric power is supplied to the power source circuit (not shown) through the AC inlet 46 and the main switch 26 so that respective predetermined voltages are applied to the display section 28, the pressure sensor 14, the CPU 54, the air compressor 13, the pressure control valve 38, and the discharge valve 12.

As was described above, the start and stop of the compressor 13, and the opening and closing of the pressure control valve 38 are controlled according to the pressure of the closed space measured by the pressure sensor 14, so that the pressure of the closed space can be adjusted to the set pressure. The air thus pressure-controlled can be discharged into the body cavity as the discharge valve 12 is opened. In addition, in response to the change in the set pressure, the pressure of the closed space is adjusted and thus the air discharge pressure is adjusted.

The DC fan 47 operates to take-in the outside air, and the air thus taken-in is applied to the members forming the closed space to cool heat generation sources of the members, such as the compressor, so that the temperature of the air in the closed space is maintained substantially equal to that of the outside air. This feature solves the problem that the pressure of the air in the closed space is varied by the variation in temperature inside the housing 10 when the closed space is sealed and has constant volume. Accordingly, the pressure control is stable at all times.

The circuit board K is located above the DC fan 47. Hence, even if, during the operation, the circuit board K generates heat, the closed space is not affected thereby. That is, because of the principle of thermal convection, a hot air moves upwardly, and therefore the air heated by the circuit board K is transmitted to the upper portion of the housing 10. The air heated and thus transmitted to the upper portion of the housing 10 is cooled by the housing 10 to move downwardly, or is forced toward the discharge outlet 60. Therefore, the heat from the circuit board is not transmitted to the air in the closed space, and the temperature of the air in the closed space is maintained equal to the outside temperature. Accordingly, the pressure of the air in the closed space is not changed; that is, the pressure control can be carried out stably.

The discharge outlet 60 is located at a position far from the DC fan 47 and higher than the circuit board K. Therefore, since the DC fan takes-in the outside air, the heat generated from the circuit board K is not accumulated in the inside of the housing 10 and is discharged out of the housing 10. This means that the temperature of the air in the closed space is maintained equal to the outside temperature and the stable pressure control is realized.

Since the compressor 13 is located beside the DC fan 47. Therefore, the air coming into the housing from outside strikes against the compressor 13 directly. Accordingly, with respect to the dust which is mixed with the air to be supplied to the closed space from outside, a dust-proof countermeasure should be taken mainly for the circumference of the compressor 13 against which the air strikes in the above-described manner.

When compared with the simple members forming the closed space, the parts on the circuit board K are intricate. It is preferable that maintenance of the circuit board K can be achieved with ease. In the embodiment, the circuit board K is arranged in the upper space of the housing 10, and is secured with the screws 61 only. Hence, the circuit board K can be removed with ease, so that the maintenance of the circuit board K can be achieved readily. Furthermore, the circuits on the circuit board K can be observed without movement of the circuit board K, and therefore the maintenance can be readily achieved with the circuit board K maintained fixed.

In order to move the circuit board K to confirm the members provided below the circuit board K, one side of the circuit board K may be fixed with a hinge.

As is apparent from the above description, according to the invention, the formation of the closed space makes it possible to accurately perform the pressure control according to the airs different in discharge pressure. Further, since the temperature of the air in the closed space is not greatly changed, the pressure control can be achieved stably.

What is claimed is:

1. An endoscope air sending device comprising:

a compressor which compresses air and sends the air thus compressed into a closed space;

an air tank which is a part of the closed space;

an air filter which removes dust from the closed space;

a pressure sensor which measures a pressure of the air in the closed space;

a pressure control valve which discharges the air from the closed space to adjust the pressure of the air in the closed space according to a pressure measured by the pressure sensor;

a discharge valve which discharges the air from the closed space;

an air sending fan which supplies air from outside of the endoscope air sending device to members forming the closed space;

a circuit board on which circuits for transmitting electrical signals to the compressor, the pressure sensor, the pressure control valve, and the discharge valve are provided; and a discharge outlet through which the air heated by the circuit board is discharged, and wherein the air sending fan, the compressor, the air tank, the air filter, the pressure sensor, the pressure control valve, and the discharge valve are provided below the circuit board, with the discharge outlet provided above the circuit board.

2. The endoscope air sending device according to claim 1, wherein the closed space is formed by communicating the members with one another which are the compressor, a first air tube which connects the compressor and the air tank to each other, the air tank, a second air tube which connects the air tank and the air filter to each other, the air filter, a third air tube which connects the air filter and the discharge valve to each other, a fourth air tube which connects the third air tube and the pressure control valve to each other, the pressure control valve, a fifth air tube which connect the third air tubes to the pressure sensor, the pressure sensor, and the discharge valve.

3. The endoscope air sending device according to claim 2, wherein the third air tube is communicated through couplings with the fourth air tube and the fifth air tube.

4. The endoscope air sending device according to claim 1, wherein the circuit board is supported by board supports.

5. The endoscope air sending device according to claim 1, wherein the discharge outlet is provided away from the air sending fan with respect to the closed space.

6. The endoscope air sending device according to claim 1, wherein the air sending fan is provided beside the compressor.

* * * * *